(12) United States Patent
Tian

(10) Patent No.: US 9,924,866 B2
(45) Date of Patent: Mar. 27, 2018

(54) COMPACT REMOTE EYE TRACKING SYSTEM INCLUDING DEPTH SENSING CAPACITY

(71) Applicant: Heptagon Micro Optics Pte. Ltd., Singapore (SG)

(72) Inventor: Yibin Tian, Mountain House, CA (US)

(73) Assignee: Heptagon Micro Optics Pte. Ltd., Singapore (SG)

( * ) Notice: Subject to any disclaimer, the term of this patent is extended or adjusted under 35 U.S.C. 154(b) by 0 days.

(21) Appl. No.: 15/384,609

(22) Filed: Dec. 20, 2016

(65) Prior Publication Data

US 2017/0196451 A1 Jul. 13, 2017

Related U.S. Application Data

(60) Provisional application No. 62/277,108, filed on Jan. 11, 2016.

(51) Int. Cl.

| A61B 3/113 | (2006.01) |
|---|---|
| A61B 3/00 | (2006.01) |
| G06K 9/00 | (2006.01) |
| G06T 7/50 | (2017.01) |
| G01B 11/22 | (2006.01) |

(52) U.S. Cl.
CPC ............ *A61B 3/113* (2013.01); *A61B 3/0025* (2013.01); *G01B 11/22* (2013.01); *G06K 9/0061* (2013.01); *G06K 9/00201* (2013.01); *G06K 9/00228* (2013.01); *G06K 9/00604* (2013.01); *G06T 7/50* (2017.01); *G06T 2207/30201* (2013.01)

(58) Field of Classification Search
CPC .................... G06K 7/10762; G06K 9/00335
USPC .................. 351/209, 210, 221, 246; 382/103
See application file for complete search history.

(56) References Cited

U.S. PATENT DOCUMENTS

| 8,474,976 B2 | 7/2013 | Duong et al. |
|---|---|---|
| 8,885,882 B1 | 11/2014 | Yin et al. |
| 8,908,917 B2 | 12/2014 | Durrell et al. |
| 8,929,589 B2 | 1/2015 | Publicover et al. |
| 8,944,600 B2 | 2/2015 | Blixt et al. |
| 8,982,046 B2 | 3/2015 | Edwards et al. |
| 9,041,787 B2 | 5/2015 | Andersson et al. |
| 9,070,017 B2 | 6/2015 | Hennessey et al. |
| 9,110,504 B2 | 8/2015 | Lewis et al. |

(Continued)

*Primary Examiner* — Hung Dang
(74) *Attorney, Agent, or Firm* — Fish & Richardson P.C.

(57) ABSTRACT

The present disclosure describes compact remote eye tracking systems that include depth sensing capacity. In one aspect, a method of eye tracking includes illuminating a subject's eye with illumination; detecting, in a depth sensor, optical signals reflected from the subject's face in response to the illumination; generating a depth map based on the optical signals detected by the depth sensor; acquiring an intensity image based on optical signals reflected from the subject's face in response to the illumination; determining, based on a portion of the depth map corresponding to the subject's eye, an estimated distance between the subject's eye and a target screen; determining an estimated gaze direction of the subject's eye based on information obtained from the intensity image; and determining, based on the estimated gaze direction and the estimated distance between the subject's eye and the target screen, a gaze point for the subject's eye.

18 Claims, 8 Drawing Sheets

(56) References Cited

U.S. PATENT DOCUMENTS 9,135,508 B2 9/2015 Vaught et al.
2013/0107214 A1* 5/2013 Blixt ...................... A61B 3/113
351/210

* cited by examiner

COMPACT REMOTE EYE TRACKING SYSTEM INCLUDING DEPTH SENSING CAPACITY

FIELD OF THE DISCLOSURE

The present disclosure relates to compact remote eye tracking systems that include depth sensing capacity.

BACKGROUND

Eye tracking refers to the process of determining eye movement and/or gaze point. Eye tracking is widely used, for example, in psychology and neuroscience, medical diagnosis, marketing, product and/or user interface design, and human-computer interactions. Some eye tracking methods use search coils, electrooculogram, or special contact lens. These methods are considered to be intrusive as the eye trackers need to be in contact with the subject's eyes or the face regions surrounding the eyes.

Non-contact optical methods also have been developed for eye tracking. For example, light (e.g., infrared) can be directed to, and reflected by, the eye and sensed by a video camera or other optical sensor. The images or signals are analyzed to extract eye movement information. Video-based eye trackers usually utilize the corneal reflection and the center of the pupil, although some optical methods for eye tracking utilize image features from inside the eye, such as the retinal blood vessels. Corneal reflection and pupil center based eye tracking methods are widely used because they are non-invasive and relatively inexpensive.

Eye tracking methods also can be divided into two categories: head-mounted and remote. Head-mounted eye trackers are worn on the subject's head, whereas remote eye trackers are placed at a certain distance from the subject, for example, on a table or computer display.

The present disclosure relates to remote eye tracking, utilizing corneal reflection and pupil center. It is assumed there is a target screen plane at which the subject is looking (e.g., television screen, computer screen, electronic tablet or smart phone display).

FIG. 1A illustrates an example of a remote eye tracker utilizing corneal reflection and pupil center. Each illuminator 20 forms a bright spot in the image of the eye obtained by the camera 22 as a result of corneal reflection (see FIG. 1B). Each illuminator 20 can comprise a light source and may consist of multiple light emitting elements placed next to each other. If the subject's head is at a fixed pose, the direction of the subject's gaze can be determined by the vector formed between the center of corneal reflection and the center of pupil (see "OG" in FIG. 1(c)), which can be mapped to a target screen. Thus the coordinates of the gaze point (G) can be determined using the horizontal and vertical components of the gaze direction and its distance from the subject's eye 24.

Using two or more illuminators 20 in video eye trackers can be advantageous for several reasons. First, when there is head movement during eye tracking, the gaze direction is dependent on the head pose, in addition to the pupil center and corneal reflection. Multiple corneal reflections from the illuminators provides additional information from which head pose can be determined, and thus allow head movements during eye tracking.

Further, the separation between the corneal reflections appearing on the image (FIG. 1B) sensed by the camera 22 is a function of the distance (D) between the eye and the eye tracker. For a given camera-illuminator configuration, the corneal reflection separation in the image becomes smaller when the eye is further away from the eye tracker. Thus the eye to eye tracker distance (D) can be estimated from the corneal reflection separation. In general, as the eye to eye tracker distance (D) increases, the corneal reflection separation becomes less sensitive (i.e., diminishing differentiation power). In such instances, it is necessary to increase the illuminator separation (L) for larger eye to eye tracker distance (D). The illuminator separation (L), however, is one of the main factors affecting the size (e.g., length) of a remote video eye tracker.

SUMMARY

The present disclosure describes compact remote eye tracking systems that include depth sensing capacity.

For example, in one aspect, this disclosure describes a method of eye tracking including illuminating a subject's eye with illumination. The method includes detecting, in a depth sensor, optical signals reflected from the subject's face in response to the illumination, generating a depth map based on the optical signals detected by the depth sensor, and acquiring an intensity image based on optical signals reflected from the subject's face in response to the illumination. The method further includes determining, based on a portion of the depth map corresponding to the subject's eye, an estimated distance between the subject's eye and a target screen, determining an estimated gaze direction of the subject's eye based on information obtained from the intensity image, and determining, based on the estimated gaze direction and the estimated distance between the subject's eye and the target screen, a gaze point for the subject's eye.

In another aspect, this disclosure describes an eye tracking apparatus that includes an illuminator operable to illuminate a subject's eye with illumination. The apparatus includes a depth sensor operable to detect optical signals reflected from the subject's face in response to the illumination, and an image sensor operable to acquire an intensity image based on optical signals reflected from the subject's face in response to the illumination. The apparatus also includes one or more processors configured to generate a depth map based on the optical signals detected by the depth sensor, determine, based on a portion of the depth map corresponding to the subject's eye, an estimated distance between the subject's eye and a target screen, determine an estimated gaze direction of the subject's eye based on information obtained from the intensity image, and determine, based on the estimated gaze direction and the estimated distance between the subject's eye and the target screen, a gaze point for the subject's eye.

Some implementations include one or more of the following features. For example, in some instances, the depth sensor includes a time-of-flight sensor. Further, in some cases, both of the depth sensor and the image sensor are implemented by the same time-of-flight sensor. In some instances, the image sensor is implemented by an infra-red camera different from the depth sensor.

In some implementations, integration timing of the depth sensor and the infra-red camera can be correlated to timing of the illumination by the illuminator. The processor(s) can be configured to apply a face segmentation to identify a portion of the intensity image representing the subject's eye, and to determine which signals acquired by the depth sensor correspond to the subject's eye based on a mapping between pixels of the depth sensor and pixels of the infra-red camera. The processor(s) also can be configured to determine the estimated gaze direction of the subject's eye using an estimated pupil center and an estimated corneal reflection obtained from information in the intensity image.

In some implementations, a controller is configured to control a field of the illumination by the illuminator dynamically based on a location and distance of the subject's face and/or eye as determined in one or more previous frames.

Some implementations can provide a relatively compact eye tracker that obviates one or more of the difficulties encountered in known eye tracking systems. Further, in some cases, the eye tracker can be implemented as a module having much smaller dimensions (e.g., half the size) as compared to prior eye-tracking modules.

Other aspects, features and advantages will be apparent from the following detailed description, the accompanying drawings and the claims.

DETAILED DESCRIPTION

Figure 1A:
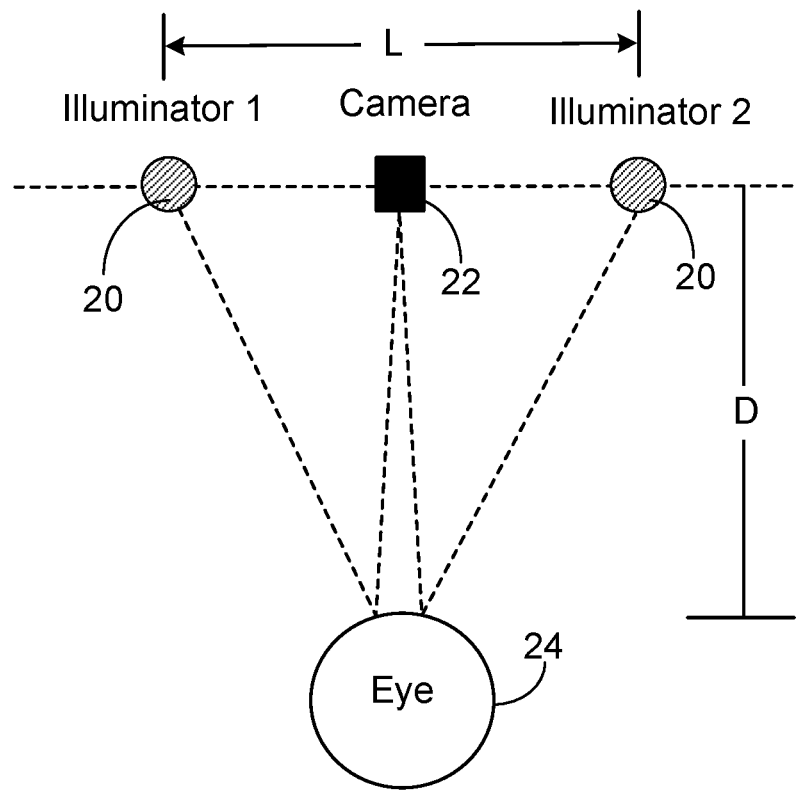
FIG. 1A illustrates an example of a remote eye tracking system.
Figure 1B:
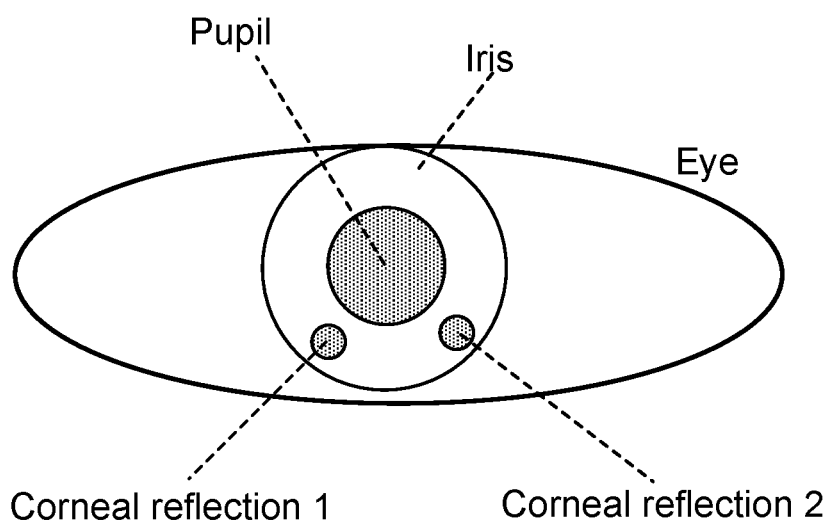
FIG. 1B illustrates an image acquired by the camera in the remote eye tracker of FIG. 1A.
Figure 1C:
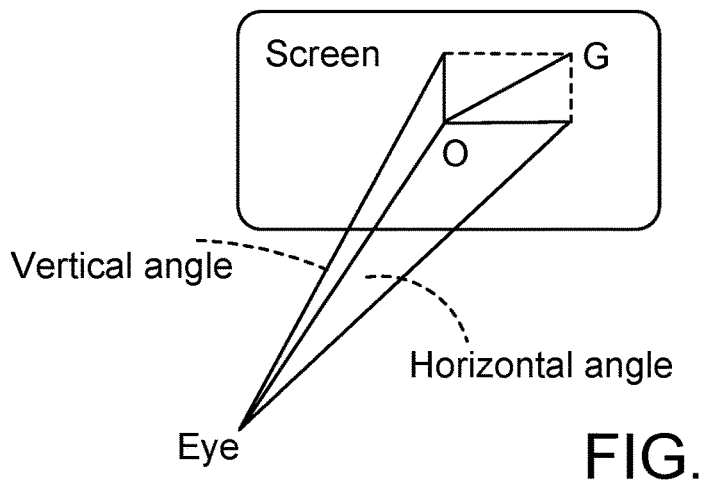
FIG. 1C illustrates geometrical relationships for the remote eye tracker of FIG. 1A.
Figure 2:
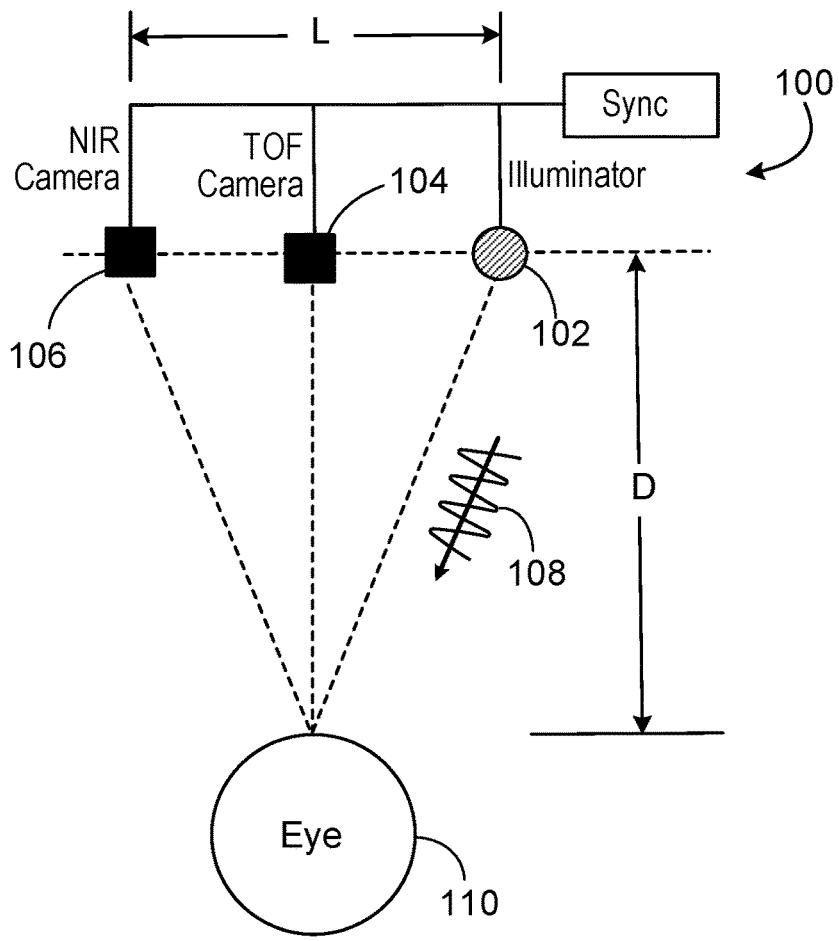
FIG. 2 illustrates an example of an eye tracking system.

As shown in FIG. 2, a remote eye tracker 100 includes an illuminator 102 that is operable to emit light (e.g., infra-red) toward a subject's face including the subject's eye 110. The illuminator 102 emits homogenous illumination 108 of a specific wavelength and can be modulated, for example, at a relatively high frequency (e.g., 10-100 MHz). The eye tracker 100 also includes a depth sensor such as an optical time-of-flight (TOF) sensor 104 that can detect optical signals indicative of distance to the subject's eye 110. The TOF sensor 104 is operable to demodulate the acquired signals and to generate depth data. Thus, the TOF sensor 104 provides depth sensing capability for the eye tracker 100. The eye tracker 100 of FIG. 1 further includes an infra-red (IR) image sensor, such as a near-IR (NIR) camera 106, which is operable to acquire an intensity image of the subject's eye 110. The image sensor 106 can be implemented, for example, as a CMOS or CCD camera. The TOF sensor 104 and NIR camera 106 are operable to detect light having the same wavelength as the illumination 108 generated by the illuminator 102.

Preferably, the optical axes of the illuminator 102 and the NIR camera 106 should be positioned such that there is an angle between them of no less than about five degrees. Under such conditions, the pupil of the subject's eye appears as a black circle or ellipse in the image of the eye acquired by the NIR camera 106. It also helps reduce the impact of specular reflections from spectacles or contact lens worn by the subject.

Figure 3:
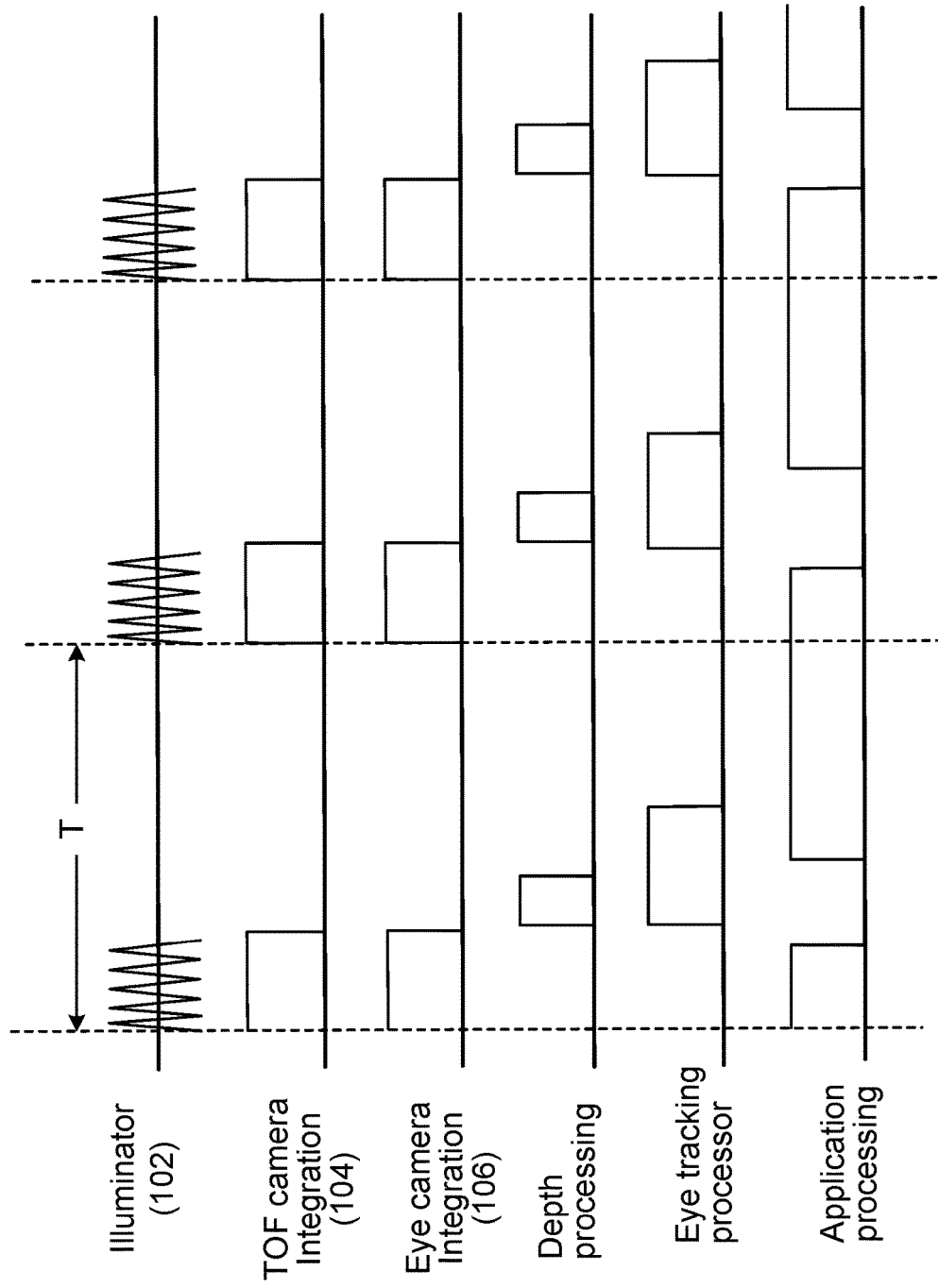
FIG. 3 is an example of a timing diagram for the eye tracking system of FIG. 2.

Operations of both the NIR camera 106 and TOF sensor 104 are synchronized with the illuminator 102 such that their integration timings are correlated to the timing of the illuminator 102. An example of the timing is illustrated in FIG. 3.

Figure 4:
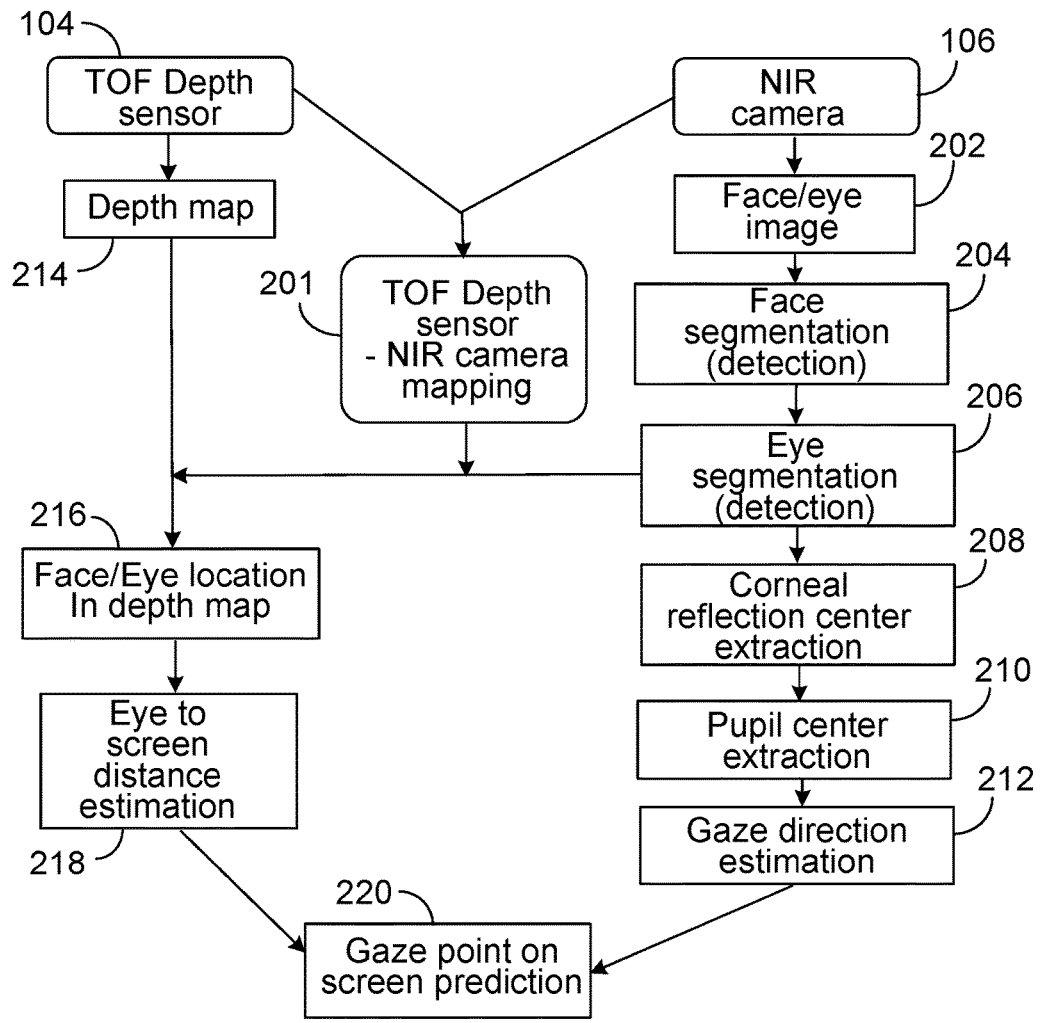
FIG. 4 is a flow chart showing an example of a method for eye tracking using depth sensing.

A method of determining a subject's gaze point on the target screen (e.g., television screen, computer screen, electronic tablet or smart phone display) is described with respect to FIGS. 2 and 4. Preferably, the TOF sensor 104 and NIR camera 106 are calibrated so that geometric relationships are established between a depth map subsequently generated from the signals acquired by the TOF sensor 104, on the one hand, and an image acquired by the NIR camera 106:

$$q(u,v)=f\{p(x,y)\},$$

where (u, v) and (x, y) are the pixel coordinates of point q and p in the TOF sensor 104 and NIR camera 106, respectively. This provides a mapping between pixels of the TOF sensor 104 and pixels of the NIR camera 106 (see 201 in FIG. 4).

When the subject's face (including the subject's eye 110) is illuminated by the illumination 108, light reflected by the subject's face is sensed by the TOF sensor 104 and the NIR camera 106. The eye's cornea is highly reflective (i.e., spectrally reflective), and thus the homogenous illumination from the illuminator 102 reflects from the eye's cornea as a dot. The reflected dot is incident on, and sensed by, the TOF sensor 104 and the NIR camera 106. Other parts of the subject's face are diffusively reflective, and thus are not as reflective as the subject's eye 110. The NIR camera 106 acquires an image of the subject's face, including the eye 110 (see 202 in FIG. 4).

The process of FIG. 4 then applies a face segmentation technique to detect the portion of the image representing the eye 110 (see 204 in FIG. 4) and an eye segmentation technique to detect the portion of the image representing the eye's cornea (see 206 in FIG. 4). Known techniques can be used for the face segmentation and eye segmentation. For example, in some cases, eye segmentation segments the image of the subject's eye into a multitude of features according to a segmentation model that includes the subject's eye and the region around the subject's eye.

The process continues by estimating the center of the corneal reflection (208 in FIG. 4) and estimating the center of the eye's pupil (210 in FIG. 4). The process uses the estimated pupil center and the estimated corneal reflection to determine an estimated gaze direction of the subject's eye (see 212 in FIG. 4). The estimated gaze line, which sometimes is referred to as a gaze vector or line of sight, runs from the cornea center through the pupil center. In particular, by analyzing the geometry and orientation of the subject's eye as captured in the image, the process estimates a gaze direction indicating where the subject's eye is looking. In some instances, the estimated gaze is adjusted based on eye tracker calibration.

Figure 5:
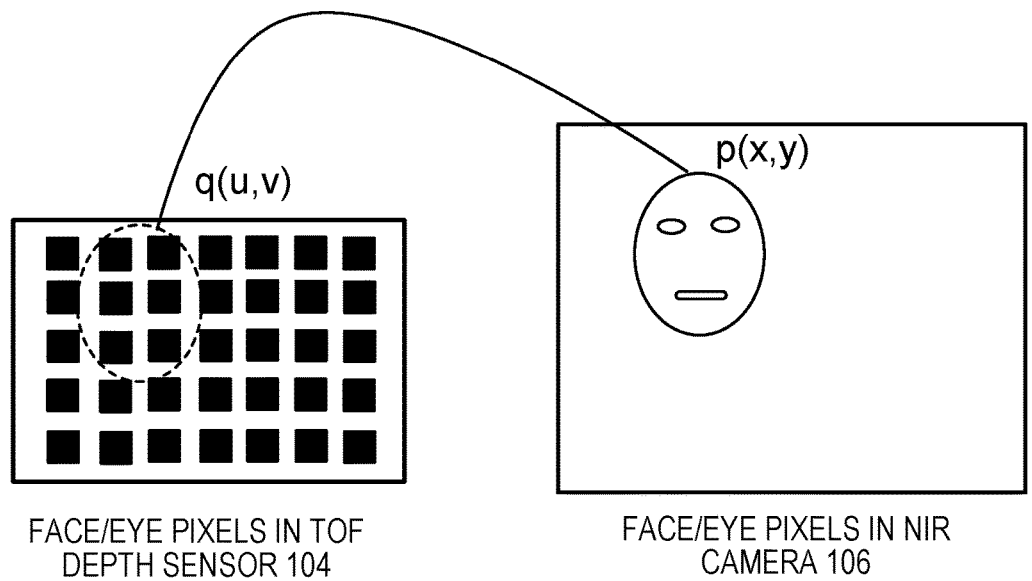
FIG. 5 illustrates an example of mapping pixels from an infra-red camera to a time-of-flight depth sensor.

In parallel with performance of the foregoing steps, the process generates a depth map based on the signals acquired by the TOF sensor 104 (see 214 in FIG. 4). Next, the process determines which signals acquired by the TOF depth sensor 104 correspond to the subject's face, including the subject's eye 110 (see 216 in FIG. 4). To accomplish this, the process uses the mapping between the TOF sensor pixels and the IR camera pixels (201) and the output of the face and/or eye segmentations (204, 206). Thus, the locations of the subject's face and eye obtained from the face and eye detection carried out on the image from the NIR camera 106 are mapped to the depth map generated from the signals sensed by the TOF sensor 104. FIG. 5 illustrates graphically an example of the mapping between the portion of the image of the subject's face acquired by the NIR camera 106 and the corresponding part of the depth map based on the TOF sensor 104.

The process then proceeds to determine, based on the portion of the depth map corresponding to the subject's eye 110, an estimate of the distance between the subject's eye 110 and the target screen (see 218 in FIG. 4). Next, the process predicts the subject's gaze point on the target screen (see 220 in FIG. 4) based on the target-screen eye distance (from 218) and the estimated gaze direction (from 212).

If the subject's head moves during the eye tracking process, the gaze direction also is dependent on the head pose. In that case, the depth map information for the subject's face and/or eyes in 216 can be used to estimate the subject's head pose, which then can be provided as further input for estimating the gaze direction in 212.

Additional details for some implementations of the eye tracker are described in the following paragraphs.

Figure 6A:
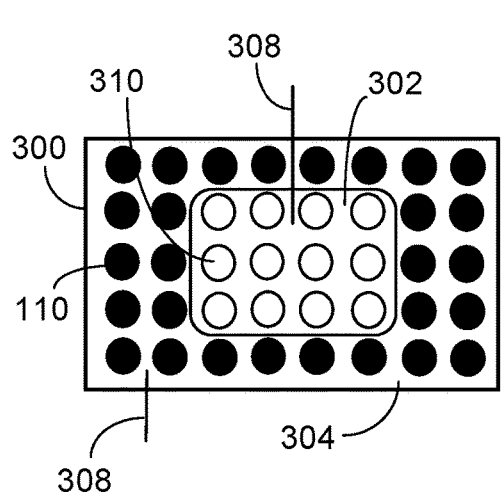
FIGS. 6A and 6B illustrate examples of arrangement of light emitting elements in an illuminator.
Figure 6B:
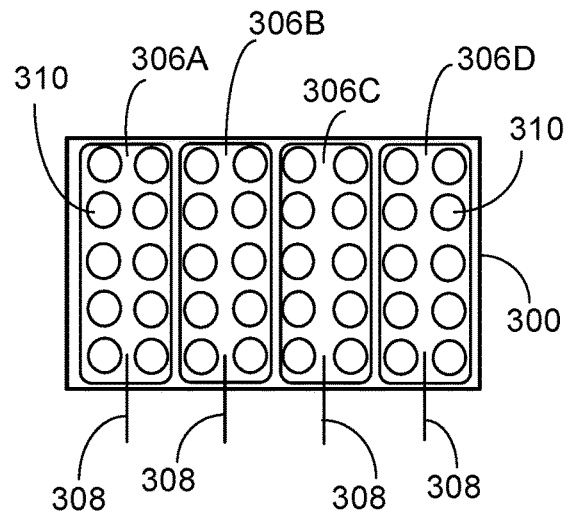

The illuminator 102 can include one or more light emitter such as light-emitting diodes (LEDs) or vertical-cavity surface-emitting lasers (VCSELs). In some cases, one illuminator 102 includes an array of light emitting elements and a beam shaping structure (such as lens) to shape the field of illumination. The light emitting elements can be arranged in such a way that dynamic control of the field of illumination is possible. For example, as shown in FIG. 6A, either central section 302 or the entire light emitter array (i.e., central section 302 and peripheral section 304) can be enabled. On the other hand, in the example of FIG. 6B, various combinations of sections 306A, 306B 306C, 306D of the array 300 can be enabled. Thus, in some instances, only two of the sections (e.g., 306A and 306B; or 306B and 306C) of the array 100 are enabled, whereas in other instances, only three of the sections (e.g., 306A, 306B and 306C; or 306A, 306B and 306D) of the array 100 are enabled. In some cases, the entire array is enabled. A respective electrical supply line 308 is provided for the light emitting elements 110 in each section of the array. The decision as to which sections of the array 100 to enable under such dynamic control can be based on the location and distance of the face and/or eyes as determined from one or more previous frames. A controller (e.g., a microcontroller or other control circuitry) can be included to provide the feedback for dynamic control of the field of illumination.

In some implementations, for each frame during a period of time T, the illuminator 102 is on (i.e., emits illumination 108) only for a fraction of the time T. Further, in some cases, the intensity of illumination 108 is adjusted dynamically based on the eye-to-screen distance measurements from previous frames. For example, a higher intensity can be generated for larger distances D, whereas lower intensities can be generated for smaller distances D. The intensity adjustments can be achieved by changing the electrical current level to the light emitters in the illuminator 102. In some instances, these features can help optimize, and thereby reduce, the power consumption of the illuminator 102.

The number of prior frames used to estimate the light emitting sections to be enabled, as well as the illumination levels, can be determined, for example, based on expected head motions and distance ranges in a specific application. In some implementations, using one to three prior frames can achieve suitable results.

For safety and power consumption considerations, the illuminator 102 and the eye tracking system should be configured to shut off automatically if it is determined the subject's face/eye is too close to the eye tracker (e.g., within 10 cm).

The field of illumination should be matched closely to the field of views of both the NIR camera 106 and TOF sensor 104. In some cases, it is desirable to provide a rectangular field of illumination with the long edge along the horizontal direction and the short edge along the vertical direction because head movements tend to be more significant and frequent in the horizontal direction than in the vertical direction.

When the process determines which signals acquired by the TOF depth sensor 104 correspond to the subject's face 110 (see 216 in FIG. 4), it sometimes is desirable to exclude certain pixels from the determination. For example, pixels near the boundary of the face/eye portion of the depth map may represent mixed signals from both the face/eye and the more distant background. Such pixels should be excluded when the eye-to-screen distance (D) is estimated at 218 (FIG. 4).

In some cases, a confidence level is derived for depth measurement of each pixel in the depth sensor 104. Depth pixels with low confidence levels, even though they are located within the face/eye region, can be excluded for eye-to-screen distance estimation. When the depth sensor resolution is low (e.g., when the number of pixels is low), it is preferable to use the face region to estimate the eye-to-screen distance (D). Otherwise, it is preferable to the eye region alone, which can provide a more accurate estimation in many situations.

In some implementations, the gaze direction estimation is performed in two stages by machine learning. For example, a large set of pre-collected eye depth maps and corresponding eye images (or particular features thereof) are used to train a neural network or support vector machine such that an implicit model is established in the neural network or support vector machine. During eye tracking, a new eye depth map and corresponding eye image (or the same features thereof as used in the training stage) are provide to the trained neural network or support vector machine for it to make a prediction of the gaze direction. The training stage typically can be performed once for the eye tracking system.

As described above, the implementation of FIG. 2 includes two cameras (i.e., the TOF sensor 104 and the NIR camera 106). In some implementations, however, as shown in FIG. 6, a single TOF camera 104 is used to provide an intensity image as well as the depth information. In this case, the resolution of the TOF camera 104 should be high enough such that its intensity image can be used instead of an image from the NIR camera 106 of FIG. 2.

Figure 7:
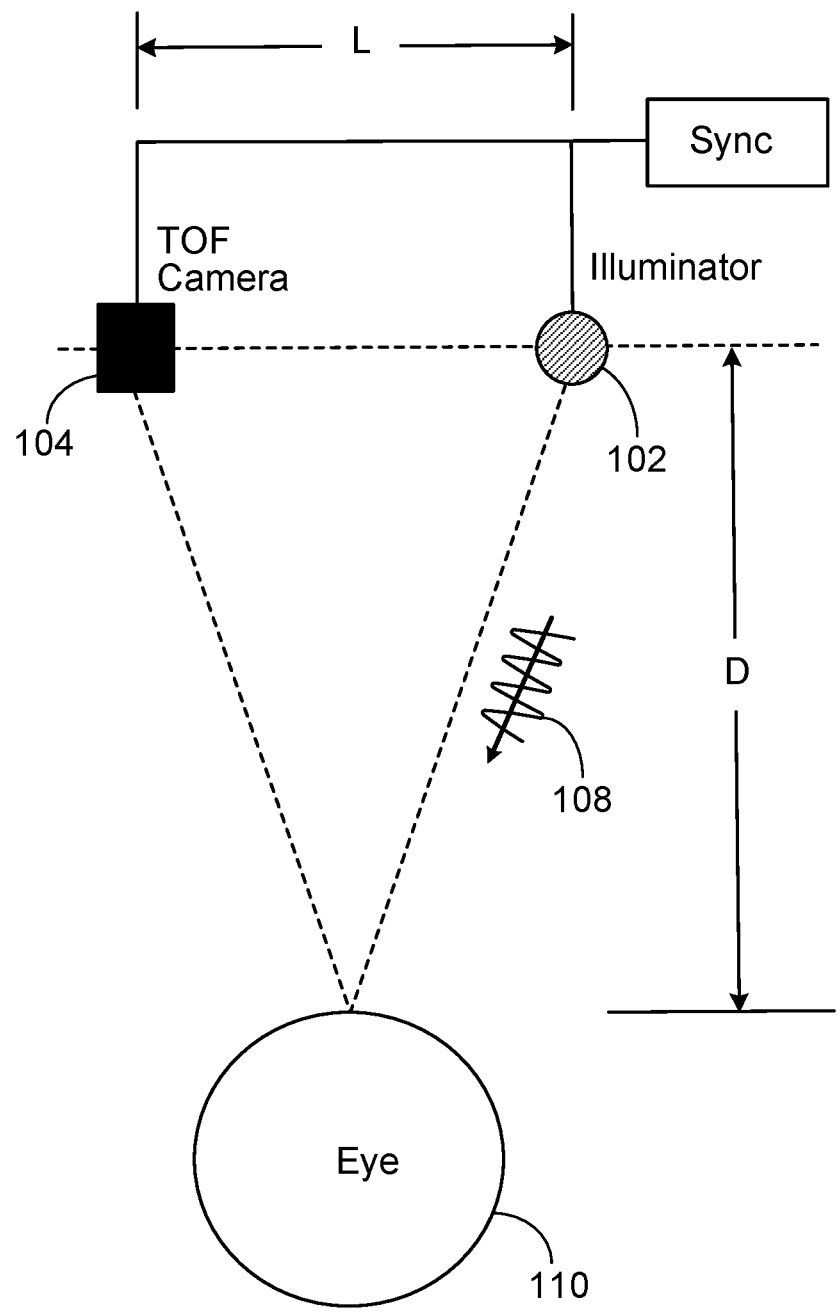
FIG. 7 illustrates an example of an eye tracking system.
Figure 8:
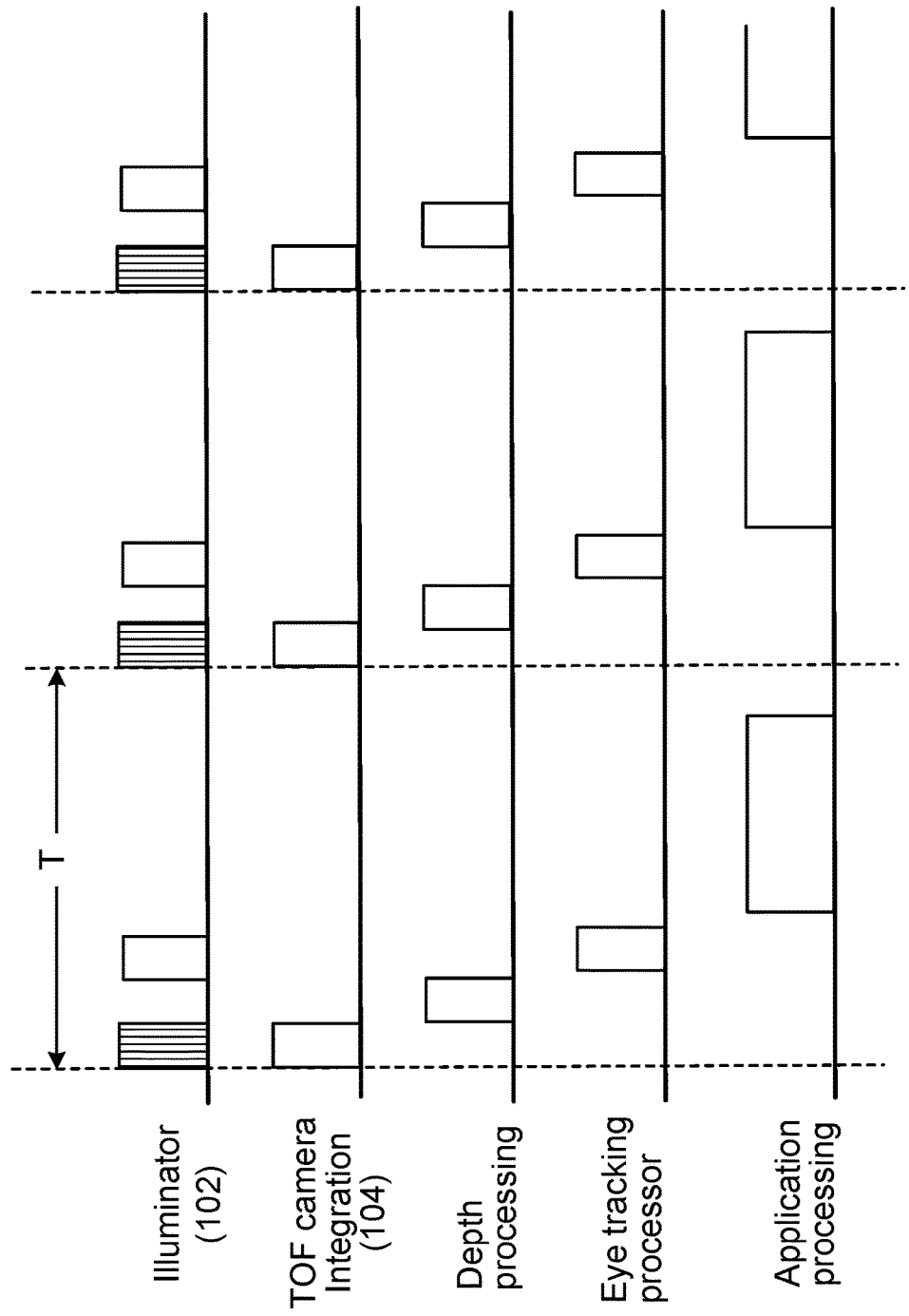
FIG. 8 is an example of a timing diagram for the eye tracking system of FIG. 7.

In the n-phase TOF camera 104 of FIG. 6, the intensity image (B) can be calculated as follows:

$$B = \sqrt{(P_1)^2 + (P_2)^2 + \ldots + (P_n)^2}$$

where $(P_i)^2$ (for i=1, 2, ... n) is the intensity at an individual phase. For eye tracking purpose, the pixel values of this intensity image (B) are adjusted using the corresponding distance image, as well as the illumination profile and camera vignette profile. The latter two characteristics are constant for a give TOF camera and can be obtained, for example, during camera characterization. Operations of the TOF sensor 104 of FIG. 6 is synchronized with the illuminator 102 such that the integration timing is correlated to the timing of the illuminator 102. An example of the timing is illustrated in FIG. 7. Also, in the implementation of FIG. 6, the depth map and face/eye intensity image are already perfectly aligned. Thus, $$q(u,v)=p(x,y).$$

Various implementations described here can be realized in digital electronic circuitry, integrated circuitry, specially designed ASICs (application specific integrated circuits), computer hardware, firmware, software, and/or combinations thereof. These various implementations can include implementations in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Figure 9:
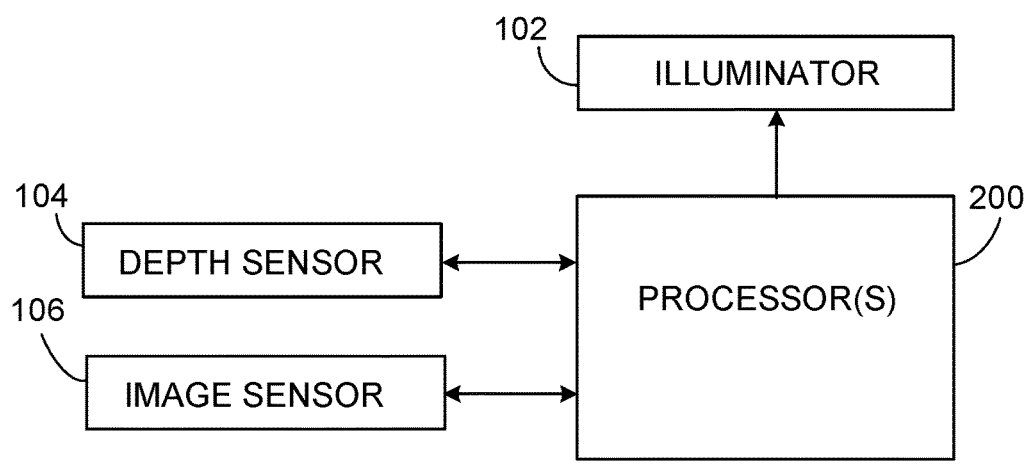
FIG. 9 illustrates an example of an eye tracking system.

Thus, as shown in FIG. 9, in some cases, one or more processors (e.g., microprocessor or microcontroller) 200 are programmed or otherwise configured to control the illuminator 102, receive signals generated by the TOF sensor 104 and NIR camera 106, and process the signals, for example, in accordance with the method of FIG. 4 so as to generate the gaze point prediction.

The calculated gaze point can be used, for example, as input for various applications (e.g., diagnostic, human performance and/or control applications). Particular examples include assessing the effectiveness of television advertising or web-page designs by measuring ocular dwell times, monitoring the degree of fatigue of an individual, tracking human performance with age, determining the effectiveness of training or exercise on performance, assessing driver or pilot awareness, assessing effects of drugs or alcohol on an individual, diagnosing post-traumatic stress disorder, magnifying or changing the brightness of specific objects or images under observation, controlling aspects of games, diagnosing and monitoring degenerative eye conditions, allowing individuals with limited or no mobility below the neck to communicate by controlling a computer cursor using one or more eyes and eyelids, and acquiring foundational clinical data to assess neurological or cognitive disorders. The eye tracking systems and methods described above can be used in any of these applications, as well as others. In particular, output generated by the eye tracking system or eye tracking method can be used in any of the foregoing applications.

As will be readily apparent, various modifications can be made to the foregoing examples within the spirit of the invention. For example, in some instances, some processes or steps may be omitted. Further, in some cases, additional processes or steps may be performed. Other modifications may be made as well. Thus, other implementations are within the scope of the claims.

What is claimed is:

1. A method of eye tracking comprising:
    illuminating a subject's eye with illumination;
    detecting, in a depth sensor, optical signals reflected from the subject's face in response to the illumination;
    generating a depth map based on the optical signals detected by the depth sensor;
    acquiring an intensity image based on optical signals reflected from the subject's face in response to the illumination;
    determining, based on a portion of the depth map corresponding to the subject's eye, an estimated distance between the subject's eye and a target screen;
    determining an estimated gaze direction of the subject's eye based on information obtained from the intensity image; and
    determining, based on the estimated gaze direction and the estimated distance between the subject's eye and the target screen, a gaze point for the subject's eye.

2. The method of claim 1 including acquiring the intensity image using the depth sensor.

3. The method of claim 1 wherein integration timing of the depth sensor is correlated to timing of the illumination.

4. The method of claim 1 including acquiring the intensity image using an infra-red camera different from the depth sensor.

5. The method of claim 4 including:
    applying a face segmentation to identify a portion of the intensity image representing the subject's eye; and
    determining which signals acquired by the depth sensor correspond to the subject's eye based on a mapping between pixels of the depth sensor and pixels of the infra-red camera.

6. The method of claim 4 wherein integration timings of the depth sensor and the infra-red camera are correlated with timing of the illumination.

7. The method of claim 1 including determining the estimated gaze direction of the subject's eye using an estimated pupil center and an estimated corneal reflection obtained from information in the intensity image.

8. The method of claim 1 wherein the depth sensor comprises a time-of-flight sensor.

9. The method of claim 1 including dynamically controlling a field of the illumination based on a location and distance of the subject's face and/or eyes as determined in one or more previous frames.

10. An eye tracking apparatus comprising:
    an illuminator operable to illuminate a subject's eye with illumination;
    a depth sensor operable to detect optical signals reflected from the subject's face in response to the illumination;
    an image sensor operable to acquire an intensity image based on optical signals reflected from the subject's face in response to the illumination; and
    one or more processors configured to:
        generate a depth map based on the optical signals detected by the depth sensor;
        determine, based on a portion of the depth map corresponding to the subject's eye, an estimated distance between the subject's eye and a target screen;
        determine an estimated gaze direction of the subject's eye based on information obtained from the intensity image; and determine, based on the estimated gaze direction and the estimated distance between the subject's eye and the target screen, a gaze point for the subject's eye.

11. The eye tracking apparatus of claim 10 wherein the depth sensor comprises a time-of-flight sensor.

12. The apparatus of claim 11 wherein the one or more processors are configured to:
   determine the estimated gaze direction of the subject's eye using an estimated pupil center and an estimated corneal reflection obtained from information in the intensity image.

13. The apparatus of claim 11 including a controller configured to control a field of the illumination by the illuminator dynamically based on a location and distance of the subject's face and/or eye as determined in one or more previous frames.

14. The eye tracking apparatus of claim 10 wherein both of the depth sensor and the image sensor are implemented by a same time-of-flight sensor.

15. The apparatus of claim 10 wherein integration timing of the depth sensor is correlated to timing of the illumination by the illuminator.

16. The apparatus of claim 10 wherein the image sensor is implemented by an infra-red camera different from the depth sensor.

17. The apparatus of claim 16 wherein the one or more processors are configured to:
   apply a face segmentation to identify a portion of the intensity image representing the subject's eye; and
   determine which signals acquired by the depth sensor correspond to the subject's eye based on a mapping between pixels of the depth sensor and pixels of the infra-red camera.

18. The apparatus of claim 16 wherein integration timings of the depth sensor and the infra-red camera are correlated with timing of the illumination by the illuminator.

* * * * *